US009476064B2

(12) United States Patent
Roh et al.

(10) Patent No.: US 9,476,064 B2
(45) Date of Patent: Oct. 25, 2016

(54) NEURO-PROGENITOR PRODUCED FROM AN SCNT-DERIVED ES CELL

(71) Applicant: H. Bion Co., Ltd., Seoul (KR)

(72) Inventors: Sung-Il Roh, Seoul (KR); Woo-Suk Hwang, Seoul (KR); Byeong-Chun Lee, Seoul (KR); Sung-Keun Kang, Seoul (KR); Young-June Ryu, Seoul (KR); Eu-Gene Lee, Seoul (KR); Soon-Woong Kim, Seoul (KR); Dae-Kee Kwon, Seoul (KR); Hee-Sun Kwon, Seoul (KR); Ja-Min Koo, Seoul (KR); Eul-Soon Park, Chungcheongbuk-do (KR); Youn-Young Hwang, Seongnam-si (KR); Hyun-Soo Yoon, Seoul (KR); Jong-Hyuk Park, Seoul (KR); Sun-Jong Kim, Anyang-si (KR)

(73) Assignee: H BION CO., LTD., Seoul (KR)

( * ) Notice: Subject to any disclaimer, the term of this patent is extended or adjusted under 35 U.S.C. 154(b) by 186 days.

(21) Appl. No.: 14/091,106

(22) Filed: Nov. 26, 2013

(65) Prior Publication Data

US 2014/0154800 A1 Jun. 5, 2014

Related U.S. Application Data

(60) Division of application No. 13/316,199, filed on Dec. 9, 2011, now Pat. No. 8,647,872, which is a continuation of application No. 12/591,505, filed on Nov. 20, 2009, now abandoned, which is a continuation of application No. 10/584,255, filed as application No. PCT/KR2004/003528 on Dec. 30, 2004, now abandoned.

(30) Foreign Application Priority Data

Dec. 30, 2003 (KR) .................. PCT/KR2003/002899

(51) Int. Cl.
| | | |
|---|---|---|
| *C12N 15/00* | (2006.01) | |
| *C12N 15/87* | (2006.01) | |
| *C12N 5/0735* | (2010.01) | |
| *C12N 15/877* | (2010.01) | |
| *C12N 5/0797* | (2010.01) | |
| *C12N 5/0793* | (2010.01) | |

(52) U.S. Cl.
CPC ............ *C12N 15/87* (2013.01); *C12N 5/0606* (2013.01); *C12N 15/8776* (2013.01); *C12N 5/0619* (2013.01); *C12N 5/0623* (2013.01); *C12N 2500/25* (2013.01); *C12N 2500/38* (2013.01); *C12N 2501/115* (2013.01); *C12N 2501/13* (2013.01); *C12N 2501/235* (2013.01)

(58) Field of Classification Search
CPC ............ C12N 2506/02; C12N 5/0619; C12N 2501/385; C12N 5/0606; C12N 2501/115; C12N 2501/13; C12N 5/0623; C12N 2501/155; C12N 2501/41; C12N 5/0603; C12N 5/0696

See application file for complete search history.

(56) References Cited

FOREIGN PATENT DOCUMENTS

| | | |
|---|---|---|
| CN | 1429267 A | 7/2003 |
| RU | 2216591 C2 | 1/2003 |
| WO | 86/07377 | 12/1986 |
| WO | 2002/086073 | 10/2002 |

OTHER PUBLICATIONS

Carpenter et al. Enrichment of Neurons and Neural Precursors from Human Embryonic Stem Cells. Experimental Neurology, 2001, vol. 172, pp. 383-397.*
Dhara et al. Neural differentiation of human embryonic stem cells. J. Cell Biology, 2008, vol. 105, pp. 633-640.*
Bongso et al., "Isolation and culture of inner cell mass cells from human blastocysts," Human Reproduction, Nov. 9; vol. 11:2110-2117 (1994).
Chen et al., "Embryonic stem cells generated by unclear transfer of human somatic nuclei into rabbit oocytes," Cell Research, Aug. 2003, vol. 13(4), pp. 251-263.
Chinese Office Action (Feb. 18, 2008) from co-pending Chinese Appln. No. 200480039480.7.
Cibelli et al., "Somatic Cell Nuclear Transfer in Humans: Pronuclear and Early Embryonic Development," J. of Regenerative Medicine, Nov. 26; vol. 2:25-31 (2001).
Cibelli et al., "Transgenic bovine chimeric offspring produced from somatic cell-derived stemlike cells," Nat. Biotechnol., Jul.; vol. 16:642-646 (1998).
Evans et al., "Establishment in Culture of Pluripotential Cells from Mouse Embryos." Nature, Jul. 9, vol. 292:154-156 (1981).
Gurdon et al., "Nuclear reprogramming and stem cell creation," Proc. Natl. Acad. Sci., Sep. 30, 2003, vol. 100 (supple.1), pp. 11819-11822.
Hwang et al., "Evidence of a Pluripotent Human Embryonic Stem Cell Line Derived from a Cloned Blastocyst," Science, vol. 303, No. 5664, Mar. 12, 2004, pp. 1669-1674, XP002471901.
Hwang et al., "Patent-Specific Embryonic Stem Cells Derived from Human Scnt Blastocysts," Science, vol. 308, No. 5729, Jun. 17, 2005, pp. 1777-1783, XP002471902.
Kitai et al., "Recombination Signatures Distinguish Embryonic Stem Cells Derived by Parthenogenesis and Somatic Cell Nuclear Transfer," Cell Stem Cell, vol. 1, No. 3, Sep. 2007, pp. 346-352, XP02471903.

(Continued)

*Primary Examiner* — Deborah Crouch
(74) *Attorney, Agent, or Firm* — Rothwell, Figg, Ernst & Manbeck, P.C.

(57) ABSTRACT

An embryonic stem cell line derived from a nucleus-transferred oocyte prepared by transferring a nucleus of a human somatic cell into an enucleated human oocyte may differentiate into various desired cell types.

4 Claims, 11 Drawing Sheets

(56) References Cited

OTHER PUBLICATIONS

Kwun et al., "Effects of Exogenous Hexoses on Bovine in Vitro Fertilized and cloned Embryo Development: Improved Blastocyst Formation After Glucose Replacement with Fructose in a Serum-Free Culture Medium," Molecular Reproduction and Development, 65:167-174 (2003).
Lanza et al., "Human therapeutic cloning," Nat. Med., Sep.; vol. 5:975-977 (1999).
Munsie et at., "Isolation of pluripotent embryonic stem cells from reprogrammed adult mouse somatic cell nuclei," Curr. Bioi., Aug.; vol. 10:989-992 (2000).
Reubinoff et al., "Embryonic stem cell lines from human blastocysts: somatic differentiation in vitro," Nature Biotechnology, Apr. 2000, vol. 18, pp. 399-404.
Russian Office Action (Jun. 28, 2007) from co-pending Russian Appln. No. 2006127446/15(029818).
Shu, Y. et al, "Preliminary Study on Human Cumulus Cell Nuclear Transfer", Fertil. Steril., Sep. 2002, vol. 78(3), Suppl. 1, S286.
Solter, "Mammalian Cloning: Advances and Limitations," Nt. Rev. Genet., Dec.; vol. 1:199-207 (2000).
Thomson et al., "Embryonic Stem Cell Lines Derived from Human Blastocysts," Science Mag., Nov.; vol. 6; 282:1145-1147 (1998).
Thomson et al., "Isolation of a primate embryonic stem cell line," Proc. Natl. Acad. Sci. USA, Aug.; vol. 92:7844-7848 (1995).
Wakayama et al, "Differentiation of Embryonic Stem Cell Lines Generated from Adult Somatic Cells by Nuclear Transfer," Scient, Apr. 27; vol. 292:740-743 (2001).
Zhang et al., "In Vitro differentiation of transplantable neural precursors from human embryonic stem cells," Nature Biotechnology, Dec. 2001, vol. 19, pp. 1129-1133.
Stojkovic et al. Derivation of a Human Blastocyst After Heterologous Nuclear Transfer to Donated Oocytes. Reproductive BioMedicine Online. 2005, vol. 11, pp. 226-231.
Mitalipov et al. Rhesus Monkey Embryos Produced by Nuclear Transfer from Embryonic Blastomeres or Somatic Cells. Biol. Reproduct. 2002, vol. 66, pp. 1367-1373.
Byrne et al. Producing Primate Embryonic Stem Cells by Somatic Cell Nuclear Transfer. Nature. Nov. 22, 2007, pp. 497-502.
Pera et al. Human Embryonic Stem Cells. J. Cell Science. 2000, vol. 113, pp. 5-10.
Fox, B. Disgraced Cloning Pioneer Could Keep His Patents. The New Scientist, Jan. 18, 2006, pp. 1-3, http://www.newscientist.com/article/dn8601-disgraced-cloning-pioneer-could-keep-his-paten.
Tobin and Kim. Confirmation of Parthenogenetic Identity by Recombination Signature in Human Embryonic Stem Cells. Stem Cells and Development, 2013, vol. 22, pp. 1016-1017.
Stojkovic et al. Derivation, growth and applications of human embryonic stem cells. Reproduction (2004) 128 259-267.
Gardner et al. Culture of viable human blastocysts in defined sequential serum-free media. Human Reproduction, 1998, vol. 13 Supplement 3, pp. 148-159.
Gardner and Lane. Towards a single embryo transfer. Reproductive BioMedicine Online, 2003, vol. 6, pp. 470-481 www.rbmonline.com/Article/786.
Jung et al., "Epigenetic signatures of somatic cell nuclear transfer-derived embryonic stem cells", International Journal of Molecular Medicine, 28, 2011, pp. 697-704.
Kim et al., "Recombination Signatures Distinguish Embryonic Stem Cells Derived by Parthenogenesis and Somatic Cell Nuclear Transfer", Cell Stem Cell, Sep. 1, 2007, pp. 346-352.

* cited by examiner

FIG. 6A

| HumanPass<br>www.humanpass.co.kr | Humanpass,INC.<br>(158-072) 2nd floor, 86-27, Sinjeong 2-Dong,<br>Yangcheon-gu Seoul, Korea<br>TEL: +82 2 2649 2630, FAX: +82 2 2649 2648 | Certificate No :<br>( DL4748 )<br>Page( 2 )/( 5 ) |

8. Test results : DNA profiling was performed utilizing 16 STR loci for individual identification of gDNA-1, 2, 3 and 4, respectively. The results is indicated below.

(1) gDNA-1

| Name | gDNA-1 | |
|---|---|---|
| Sex | XX | |
| Locus | Allele 1 | Allele 2 |
| D8S1179 | 10 | 11 |
| D21S11 | 28 | 32.2 |
| D7S820 | 8 | 11 |
| CSF1PO | 12 | 13 |
| D3S1358 | 16 | 18 |
| TH01 | 6 | 9 |
| D13S317 | 8 | 9 |
| D16S539 | 9 | 12 |
| D2S1338 | 18 | 19 |
| D19S433 | 13 | 13.2 |
| vWA | 16 | 17 |
| TPOX | 8 | 8 |
| D18S51 | 15 | 16 |
| D5S818 | 10 | 11 |
| FGA | 21 | 23 |

Registration number HMPS-HPRF-26-05(01):2008.11.24         Humanpass.

FIG. 6B

| | Humanpass, INC. (158-072) 2nd floor, 86-27, Sinjeong 2-Dong, Yangcheon-gu Seoul, Korea TEL: +82 2 2649 2630, FAX: +82 2 2649 2648 | Certificate No : ( DL4748 ) Page( 3 )/( 5 ) |
|---|---|---|

(2) gDNA-2

| Name | gDNA-2 | |
|---|---|---|
| Sex | XX | |
| Locus | Allele 1 | Allele 2 |
| D8S1179 | 10 | 11 |
| D21S11 | 32.2 | 32.2 |
| D7S820 | 8 | 11 |
| CSF1PO | 12 | 13 |
| D3S1358 | 16 | 18 |
| TH01 | 6 | 9 |
| D13S317 | 8 | 9 |
| D16S539 | 9 | 12 |
| D2S1338 | 18 | 19 |
| D19S433 | 13 | 13 |
| vWA | 17 | 17 |
| TPOX | 8 | 8 |
| D18S51 | 15 | 16 |
| D5S818 | 10 | 11 |
| FGA | 21 | 23 |

Registration number HMPS-HPRF-26-05(01):2009.11.24            Humanpass.

FIG. 6C

| | Humanpass,INC. | Certificate No : |
|---|---|---|
| HumanPass<br>www.humanpass.co.kr | (158-072) 2nd floor, 86-27, Sinjeong 2-Dong,<br>Yangcheon-gu Seoul, Korea<br>TEL: +82 2 2649 2630, FAX: +82 2 2649 2648 | ( DL4748 )<br>Page( 4 )/( 5 ) |

(3) gDNA-3

| Name | gDNA-3 | |
|---|---|---|
| Sex | XX | |
| Locus | Allele 1 | Allele 2 |
| D8S1179 | 10 | 11 |
| D21S11 | 32.2 | 32.2 |
| D7S820 | 8 | 8 |
| CSF1PO | 12 | 13 |
| D3S1358 | 16 | 18 |
| TH01 | 6 | 9 |
| D13S317 | 8 | 9 |
| D16S539 | 9 | 12 |
| D2S1338 | 18 | 19 |
| D19S433 | 13 | 13 |
| vWA | 17 | 17 |
| TPOX | 8 | 8 |
| D18S51 | 15 | 16 |
| D5S818 | 10 | 11 |
| FGA | 21 | 23 |

Registration number HMPS-HPRF-26-05(01):2008.11.24    Humanpass.

FIG. 6D

| | Humanpass, INC. | Certificate No : |
|---|---|---|
| HumanPass www.humanpass.co.kr | (158-072) 2nd floor, 86-27, Sinjeong 2-Dong, Yangcheon-gu Seoul, Korea TEL: +82 2 2649 2630, FAX: +82 2 2649 2648 | ( DL4748 ) Page( 5 )/( 5 ) |

(4) gDNA-4

| Name | gDNA-4 | |
|---|---|---|
| Sex | XX | |
| Locus | Allele 1 | Allele 2 |
| D8S1179 | 8 | 14 |
| D21S11 | 30 | 30 |
| D7S820 | 9 | 11 |
| CSF1PO | 11 | 11 |
| D3S1358 | 13 | 16 |
| TH01 | 9.3 | 9.3 |
| D13S317 | 9 | 9 |
| D16S539 | 12 | 13 |
| D2S1338 | 18 | 24 |
| D19S433 | 12 | 15 |
| vWA | 17 | 17 |
| TPOX | 10 | 11 |
| D18S51 | 12.3 | 13 |
| D5S818 | 11 | 12 |
| FGA | 27 | 28 |

Registration number HMPS-HPRF-26-05(01):2008.11.24

Humanpass.

NEURO-PROGENITOR PRODUCED FROM AN SCNT-DERIVED ES CELL

CROSS-REFERENCE TO RELATED APPLICATION

This application is a divisional of U.S. patent application Ser. No. 13/316,199, filed on Dec. 9, 2011, which was a continuation of U.S. patent application Ser. No. 12/591,505, filed on Nov. 20, 2009 (now abandoned), which was a continuation of U.S. patent application Ser. No. 10/584,255, filed on Jun. 28, 2007 (now abandoned), which was a 35 U.S.C. §371 National Phase Entry Application from PCT/KR2004/003528, filed Dec. 30, 2004, and designating the United States, which claims priority under 35 U.S.C. §119 to PCT/KR03/002899 filed Dec. 30, 2003, which are incorporated herein in their entireties.

FIELD OF THE INVENTION

The present invention relates to an embryonic stem cell line and a method for preparing the same and, more particularly, to an embryonic stem cell line prepared by transferring a nucleus of a human somatic cell into an enucleated human oocyte, culturing the resulting nucleus-transferred oocyte to form a blastocyst, and culturing an inner cell mass isolated from the blastocyst, and a method for preparing the same.

BACKGROUND OF THE INVENTION

A stem cell is normally taken to mean an undifferentiated cell capable of differentiating into all types of mature functional cells constituting a body. For example, a hematopoietic stem cell can differentiate into various corpuscular cells. An embryonic stem (ES) cell derived from an embryo has pluripotency to differentiate and develop into all types of organs, tissues and cells that form a body.

A mouse ES cell line constructed in 1981 has provided a technique and paradigm for developing a human ES cell. The development of the ES cell has been studied using a mouse teratocarcinoma, a tumor that occurs in a gonad of a closely bred mouse strain (Evans & Kaufman, *Nature*, 292:154-156 (1981)).

Bongso et al. reported a method for culturing and maintaining cells isolated from a human embryo derived from in vitro fertilization for a short-term period (Bongso et al., *Human Reproduction*, 9:2110-2117 (1994)). The cells isolated by Bongso et al. had a morphology expected in a pluripotent stem cell; however, they could not be cultured for a long-term period apparently because a proper feeder layer was not used.

Primate ES cells have been prepared from a blastocyst of a rhesus monkey and a marmoset monkey. The primate ES cells are diploid, and very similar to a human ES cell.

The study of ES cells prepared from a monkey and a human has suggested that a pluripotent stem cell might be derived from a human blastocyst, although the ES cells from the monkey and the human are somewhat different from that of a mouse in terms of phenotype (Thomson et al., *Proc. Natl. Acad. Sci. USA*, 92:7844-7848 (1995)).

The characteristic features of human pluripotent ES cells developed by Thomson et al. in 1998 (Thomson et al., *Science*, 282:1145-1147 (1998)) are as follows:

(1) expression of stage-specific embryonic antigen-3 (SSEA-3), stage-specific embryonic antigen-4 (SSEA-4), tumor rejection antigen 1-60 (TRA-1-60), tumor rejection antigen 1-81 (TRA-1-81), and alkaline phosphatase;

(2) high telomerase activity;

(3) differentiation into three types of blastodermal cells when injected into mice;

(4) dependency on feeder cells; and (5) no response to a human leukemia inhibitory factor (hLIF).

Thomson et al. obtained the above ES cells from a blastocyst donated by a couple under sterility treatment. Specifically, a trophectoderm known to inhibit the establishment of an ES cell was removed immunosurgically, an inner cell mass (ICM) was plated on a fibroblast feeder layer derived from a mouse embryo, and the ICM was replated on another feeder layer after a short attachment and expansion period. Thomson's method was not significantly different from the mouse ES cell protocol in terms of the medium or culture system; and yet a relatively high success rate was achieved.

The isolation of human pluripotent ES cells and breakthroughs in somatic cell nuclear transfer (SCNT) in mammals (Solter, *Nat. Rev. Genet.*, 1:199-207 (2000)) have raised the possibility of performing human SCNT to generate virtually unlimited sources of undifferentiated cells for research, with potential applications in tissue repair and transplantation medicine. This concept, known as "therapeutic cloning," employs a nuclear transfer of a somatic cell into an enucleated oocyte (Lanza et al., *Nat. Med.*, 5:975-977 (1999)). Previous studies on such therapeutic cloning dealt with the production of bovine ES-like cells (Cibelli et al., *Nat. Biotechnol.*, 16:642-646 (1998)) and mouse ES cells from ICMs of cloned blastocysts (Munsie et al., *Curr. Biol.*, 10:989-992 (2000); Wakayama et al., *Science*, 292:740-743 (2001)) and development of cloned human embryos until 8 to 10 cell stages (Cibelli et al., *J. Regen. Med.*, 2:25-31 (2001)).

Although several reports have indicated that an ES cell line can be established by employing a non-human mammalian oocyte, no ES cell line developed from a human oocyte utilizing the nuclear transfer technology has been reported yet.

SUMMARY OF THE INVENTION

Through extensive research and development efforts, however, the present inventors have successfully established an ES cell line by culturing a nucleus-transferred human oocyte.

Accordingly, it is an object of the present invention to provide an ES cell line derived from a nucleus-transferred oocyte prepared by transferring a nucleus of a human somatic cell into an enucleated human oocyte.

It is another object of the invention to provide a method for preparing an ES cell line, comprising the steps of:

(1) culturing a human somatic cell to prepare a nuclear donor cell;

(2) enucleating a human oocyte to prepare a recipient oocyte;

(3) preparing a nucleus-transferred oocyte by transferring a nucleus of the nuclear donor cell into the recipient oocyte and fusing the nucleus of the nuclear donor cell and the recipient oocyte;

(4) subjecting the nucleus-transferred oocyte to reprogramming, activation and in vitro culturing to form a blastocyst; and (5) isolating an ICM from the blastocyst and culturing the ICM in an undifferentiated state to establish the ES cell line.

It is a further object of the invention to provide a medium suitable for an in vitro culturing of a nucleus-transferred oocyte prepared by transferring a nucleus of a human somatic cell into an enucleated human oocyte.

It is still another object of the invention to provide a nerve cell or a neuro progenitor differentiated from an ES cell line derived from a nucleus-transferred oocyte prepared by transferring a nucleus of a human somatic cell into an enucleated human oocyte.

It is a still further object of the invention to provide a method for preparing a neuro progenitor differentiated from an ES cell line derived from a nucleus-transferred oocyte prepared by transferring a nucleus of a human somatic cell into an enucleated human oocyte, comprising the steps of:

(1) culturing the ES cell line to form an embryoid body;

(2) culturing the embryoid body in the presence of an agent suitable for differentiating a cell of the embryoid body into the neuro progenitor; and (3) selecting a cell expressing a marker of the neuro progenitor and culturing the selected cell to obtain the neuro progenitor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects and features of the present invention will become apparent from the following description of the invention, when taken in conjunction with the accompanying drawings, in which:

FIGS. 6A to 6D diagrammatically summarize the results of a karyotype analysis of an ES cell line derived from a nucleus-transferred oocyte prepared in accordance with the present invention and that of a somatic cell obtained from a female, said somatic cell providing the nucleus used for establishing the ES cell line; gDNA1: Donor (blood NT-1 donor), gDNA2: 70p (passage 70 of NT-1 embryonic stem cells), gDNA3: 140p (passage 140 of NT-1 embryonic stem cell), and gDNA4: H9 (IVF-ES line);

DETAILED DESCRIPTION OF THE INVENTION

Figure 1:
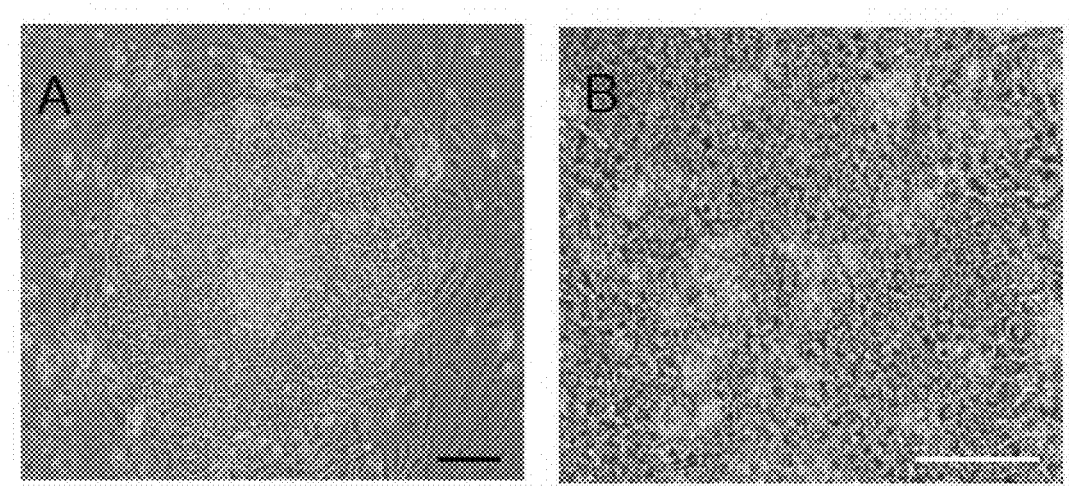
FIG. 1 shows photographs of an undifferentiated colony of ES cells derived from a nucleus-transferred oocyte in accordance with the present invention (A: ×100, B: ×200)

The term "nuclear transfer" as used herein means a process of transferring a nucleus of a somatic cell (or referred to as "nuclear donor cell") into an enucleated oocyte (or referred to as "recipient oocyte"). The resulting cell obtained by the nuclear transfer is referred to as a "nucleus-transferred oocyte" or "nuclear transfer oocyte." The term "somatic cell" as used herein means any cell constituting a body that has two sets of chromosomes (2n), excluding a germ cell that has a single set of chromosomes (n).

The term "autologous nucleus-transferred oocyte" used herein means a nucleus-transferred oocyte obtained by transferring a nucleus of a somatic cell into an enucleated oocyte where the somatic cell is isolated from a human who is expected to receive a stem cell derived from the nucleus-transferred oocyte, or a specific cell or tissue differentiated from the stem cell.

Accordingly, one of the salient advantages or benefits to be derived from the present invention resides in the fact that the person who receives a specific cell or tissue derived from the autologous nucleus-transferred oocyte would not exhibit immunorejection or suffer adverse reaction since such cell or tissue is to carry the genetic characteristics of the person.

The term "embryonic stem cell (ES cell)" means an undifferentiated cell derived from an embryo, which has the capability of differentiating into various types of mature cells. Here, "embryo" means a fertilized egg up to eight (8) weeks after its fertilization or a nucleus-transferred oocyte in the corresponding developmental stage. An embryo is created by a repetitive division of such fertilized egg or nucleus-transferred oocyte, and comprises a blastocyst containing an ICM and an outer trophectoderm.

The term "ES cell line derived from an autologous nucleus-transferred oocyte" or "autologous nucleus-transferred ES cell line" means a stem cell line derived from an ICM isolated from an autologous nucleus-transferred oocyte.

The term "neuro progenitor" refers to cells to be differentiated into nerve cells including neurons and glia such as astrocytes, oligodendrocytes, schwann cells, satellite cells, ependymal cells and microglia.

In accordance with one aspect of the present invention, there is provided a method for preparing an ES cell line, comprising the steps of:

(1) culturing a human somatic cell to prepare a nuclear donor cell;

(2) enucleating a human oocyte to prepare a recipient oocyte;

(3) preparing a nucleus-transferred oocyte by transferring a nucleus of the nuclear donor cell into the recipient oocyte and fusing the nucleus of the nuclear donor cell and the recipient oocyte;

(4) subjecting the nucleus-transferred oocyte to reprogramming, activation and in vitro culturing to form a blastocyst; and (5) isolating an ICM from the blastocyst and culturing the ICM in an undifferentiated state to establish the ES cell line.

Hereinafter, the method for preparing an ES cell line in accordance with the present invention will be described in detail.

Step 1: Preparation of Nuclear Donor Cell

A human somatic cell is cultured to function as a nuclear donor cell.

A somatic cell from a human is amenable for such nuclear donor cell, and a nucleus thereof is transferred into an enucleated human oocyte.

There is no limitation on the type or source of the somatic cell as long as it is obtained from a human, and it is also possible to use a somatic cell obtained from an institute storing human cells for commercial purposes. Preferred exemplary somatic cells include a dermal cell, a nerve cell, a cumulus cell, an oviduct epithelial cell, and the like.

In case of preparing an autologous nucleus-transferred oocyte in accordance with the present invention, the nuclear donor cell is taken from an individual who is expected to receive a stem cell derived from the nucleus-transferred oocyte, or a specific cell or tissue differentiated from the stem cell.

The somatic cell can be cultured to establish a cell line by using the Mather and Barnes method (Animal Cell Culture Methods: vol. 57 of Methods in Cell Biology (Mather & Barnes eds., Academic Press, 1998)).

In accordance with a preferred embodiment of the present invention, a uterus fluid and a phosphate buffered saline (PBS) containing P/S antibiotic (penicillin 10,000 IU, streptomycin 10 mg) are added to a somatic cell. Such somatic cell is centrifuged and washed, and cultured in a DMEM medium containing human serum, nonessential amino acids (NEAAs) and the P/S antibiotic at, e.g., 39° C. in 5% $CO_2$ atmosphere.

Especially, in case of using a cumulus cell as a nuclear donor cell, the cumulus cell can be prepared by treating a cumulus-oocyte complex with hyaluronidase to isolate a cumulus cell layer surrounding an oocyte, adding a trypsin-EDTA solution to the cumulus cell layer and placing the resulting solution at, e.g., 39° C. in 5% $CO_2$ atmosphere under saturated humidity. After centrifuging and washing, the collected cumulus cells can be cultured under the same condition described above.

Step 2: Preparation of Recipient Oocyte

A recipient oocyte as used in the present invention means an oocyte that lacks its own nucleus and receives a foreign nucleus from a human somatic cell.

A mature oocyte may be prepared by collecting a superovulated oocyte from a human ovary or obtaining an oocyte from an institute storing human oocytes for commercial purposes and culturing the oocyte using a method known in the art (Yuzpe et al., *J. Reprod. Med.*, 34:937-942 (1989)). For example, an oocyte may be matured by culturing the oocyte in the G1.2 medium, marketed by Vitro Life of Goteborg, Sweden, supplemented with 5% human serum albumin (HSA) under the condition of, e.g., 5% $CO_2$ for 4 hours.

Next, an enucleated recipient oocyte is prepared by removing the surrounding cumulus cells from the oocyte, and eliminating part of the zona pellucida and the cytoplasm containing the first polar body.

In accordance with a preferred embodiment of the present invention, the enucleation process is performed as follows.

A mature oocyte is placed in a washing solution containing hyaluronidase, and the cumulus cell is physically removed. Next, the mature oocyte is washed with the G1.2 medium. Subsequently, the zona pellucida of the oocyte is penetrated to form a small hole therein. The oocyte is enucleated by removing part of the cytoplasm containing the first polar body corresponding to 10 to 15% of the total cytoplasm through the small hole. After this removal, the enucleated oocyte is washed with the G1.2 medium and placed in the G1.2 medium for culturing.

The enucleation can be confirmed by investigating cytoplasm stained with Hoechst 33342 (Sigma Co., St. Louis, Mo., U.S.A.) using a UV detector.

Step 3: Preparation of Nucleus-Transferred Oocyte and Electrofusion

The nuclear donor cell prepared by step 1 is transferred into the enucleated recipient oocyte obtained in step 2, and the nucleus-transferred oocyte is treated with electrofusion.

The nuclear transfer of a somatic cell into a recipient oocyte may be realized by transferring either the nucleus of the somatic cell or the whole somatic cell into the recipient oocyte.

In accordance with a preferred embodiment of the present invention, the nuclear transfer and electrofusion are performed as follows.

First, the enucleated oocyte is washed with the G1.2 medium. The nuclear donor cell is injected into the enucleated oocyte in a phytohemagglutin-P (PHA-P) solution via a small hole formed in the zona pellucida using a transfer pipette to produce a nucleus-transferred oocyte. Next, the resulting nucleus-transferred oocyte is washed with the G1.2 medium and placed in the same medium.

Subsequently, the nucleus-transferred oocyte is treated with electrofusion with the aid of a cell manipulator. A mannitol solution is added to the G1.2 medium containing the nucleus-transferred oocyte. The resulting mannitol solution containing the nucleus-transferred oocyte is placed between two electrodes of the cell manipulator and is positioned such that the nuclear donor cell faces the (+) electrode. The nucleus-transferred oocyte is electrofused by treating it with a direct current ranging from 0.75 to 2.00 kV/cm for 10 to 15 µs, 1 to 5 times at an interval of, e.g., 1 second.

The fused nucleus-transferred oocyte is washed with a mannitol solution and the G1.2 medium. The mannitol solution used in this step is prepared by dissolving bovine serum albumin (BSA) and mannitol in a 4-(2-hydroxyethyl)-1-perazine ethanesulfonic acid (HEPES) buffer at a pH ranging from 7.2 to 7.4

Step 4: Reprogramming, Activation and In Vitro Culturing of Nucleus-Transferred Oocyte In order to allow the nucleus-transferred oocyte prepared in step 3 to undergo a same developmental procedure as a normal fertilized oocyte formed as a result of fusion between a sperm and an oocyte, several critical factors, such as reprogramming time, activation method and in vitro culturing conditions, should be judiciously chosen.

The present invention provides unique fertilization and development procedures conducive for activating and culturing the nucleus-transferred oocyte. Specifically, the nucleus-transferred oocyte prepared by electrofusion in step 3 is subjected to reprogramming, activation, and in vitro culturing to form a blastocyst.

The reprogramming time means the time lapsed between the electrofusion and the activation, and the length of the reprogramming time may affect the developmental capacity (in particular, the blastocyst formation rate) of the nucleus-transferred oocyte. This reprogramming time is required to allow the gene expression pattern of the somatic cell to turn into one that is appropriate and necessary for the development of the nucleus-transferred oocyte. Such reprogramming time plays a critical role in chromatin remodeling, and it is known to determine the developmental competence in vivo and in vitro of the nucleus-transferred oocyte.

The reprogramming time of the present invention may be 20 hours or below, preferably, 6 hours or below, more preferably 3 hours or below, and, most preferably, about 2 hours.

After the reprogramming, the nucleus-transferred oocyte may be activated by various chemical, physical and mechanical stimuli, such as calcium ionophore, ionomycin, ethanol, Tyrode's solution (Sigma-Aldrich, St. Louis, Mo., U.S.A.) puromycin, and the like. In the present invention, it is preferable to treat the nucleus-transferred oocyte with calcium ionophore for its activation. It is more preferable to treat the nucleus-transferred oocyte with calcium ionophore and then with 6-dimethylaminopurine (6-DMAP). Specifically, the calcium ionophore may be used at a concentration ranging from 5 to 15 µM, and, preferably, about 10 µM. In addition, said 6-DMAP may be employed at a concentration ranging from 1.5 to 2.5 mM, and, preferably, about 2.0 mM. If the concentrations of the calcium ionophore and the 6-DMAP are within the above respective ranges, the nucleus-transferred oocyte may be activated effectively. Both calcium ionophore and 6-DMAP are preferably dissolved in an in vitro culture medium.

A representative example of the in vitro culture medium is the G1.2 medium (Vitro Life, Goteborg, Sweden) comprising NaCl, KCl, NaHCO$_3$, NaH$_2$PO$_4$, CaCl$_2$, sodium lactate, glucose, phenol red, BSA, kanamycin, essential amino acids (EAAs), NEAAs, and glutamine.

Further, for an efficient in vitro culturing of the nucleus-transferred oocyte, it is preferable to supplement the culture medium with various energy substrates known in the art or employ a sequential culturing system using at least two media having different compositions suitable for each stage of the embryonic development. The sequential culturing system useful in the present invention may be any one of commercially available culturing systems. Preferably, said in vitro culturing is performed by sequentially using two media having different compositions each other, such as the G1.2 and the G2.2 media (Vitro Life, Goteborg, Sweden).

Such in vitro culture medium preferably contains a human modified synthetic oviductal fluid with amino acids (hmSOFaa), which has been designated as "SNUnt-2 medium." The hmSOFaa is prepared by supplementing a modified synthetic oviductal fluid with amino acids (mSOFaa) (Choi et al., *Theriogenology*, 58:1187-1197 (2002)) with HSA and fructose instead of BSA and glucose, respectively. The mSOFaa medium has been widely used for culturing bovine embryos.

In particular, the SNUnt-2 medium comprises 95 to 110 mM NaCl; 7.0 to 7.5 mM KCl; 20 to 30 mM NaHCO$_3$; 1.0 to 1.5 mM NaH$_2$PO$_4$; 3 to 8 mM sodium lactate; 1.5 to 2.0 mM CaCl$_2$.2H$_2$O; 0.3 to 0.8 mM MgCl$_2$.6H$_2$O; 0.2 to 0.4 mM sodium pyruvate; 1.2 to 1.7 mM fructose; 6 to 10 mg/ml HSA; 0.7 to 0.8 µg/ml kanamycin; 1.5 to 3% EAAs; 0.5 to 1.5% NEAAs; 0.7 to 1.2 mM L-glutamine; and 0.3 to 0.7% a mixture of insulin, transferrin and sodium selenite. Preferably, the SNUnt-2 medium comprises the ingredients as listed in Table 1.

TABLE 1

| Ingredient | Concentration |
| --- | --- |
| NaCl | 99.1~106 mM |
| KCl | 7.2 mM |
| NaHCO$_3$ | 25 mM |
| NaH$_2$PO$_4$ | 1.2 mM |
| sodium lactate | 5 mM |
| CaCl$_2$•2H$_2$O | 1.7 mM |
| MgCl$_2$•6H$_2$O | 0.5 mM |
| sodium pyruvate | 0.3 mM |
| fructose | 1.5 mM |
| HSA | 8 mg/ml |
| kanamycin | 0.75 µg/ml |
| EAAs | 2% |
| NEAAs | 1% |
| L-glutamine | 1 mM |
| ITS* | 0.5% |

*ITS: a mixture of 1.0 g/L insulin, 0.55 g/L transferrin and 0.67 mg/L sodium selenite The sequential culturing system of the present invention may employ any combination of the different media. For example, in the two-step culturing system, the first culturing may be conducted in the G1.2 medium, and the second culturing, in the SNUnt-2 medium.

Step 5: Removal of Zona Pellucida or Part Thereof

In order to obtain an ES cell derived from the blastocyst obtained in step 4, the zona pellucida or part thereof has to be removed from the blastocyst. This removal may be carried out by using one of the methods known in the art, e.g., pronase treatment, incubation in acidic Tyrode's solution, or a physical method such as laser dissection. It is preferable to use pronase dissolved in a suitable medium such as PBS, G2 medium (Vitro Life, Goteborg, Sweden) or S2 medium (Scandinavian IVF Sciences, Goteborg, Sweden). In a preferred embodiment, pronase is dissolved in a mixture of PBS and the S2 medium at equal volumes. The blastocyst is treated with 0.1% pronase for about 1 to 2 minutes, preferably 1 to 1.5 minutes, to remove the zona pellucida therefrom.

Step 6: Removal of Trophoblast and Isolation of ICM

Once the zone pellucida is removed from the blastocyst as described above, the trophoblast is exposed. It is preferable to completely separate the trophoblast from the ICM. The trophoblast may be separated from the ICM using one of the methods known in the art, such as an immunosurgical method employing an antibody or a mechanical method using a pipette.

In a preferred embodiment, the trophoblast is removed by an immunosurgical method that treats the trophoblast with an antibody responsive to an epitope located on a surface of the trophoblast. It is more preferable to carry out the immunosurgical method together with a complement treatment. In this case, an antibody and a complement may be used independently or simultaneously. A preferred combination between the antibody and the complement may include anti-placental alkaline phosphatase antibody (anti-AP) and baby rabbit complement, or anti-human serum antibody and guinea pig complement.

The antibody and the complement may be diluted with a suitable medium such as SNUnt-2, G2.2 or S2 medium. Preferably, the anti-AP may be diluted with the S2 medium at the ratio of 1:20; and other antibodies and complements, at the ratio of 1:1.

It is preferable to treat the zona pellucida-removed blastocyst with an antibody and then with a complement. Preferably, the blastocyst may be treated with the antibody for about 30 minutes, washed with a suitable medium, e.g., SNUnt-2, G2.2 or S2 medium, and then, treated with the complement for about 30 minutes.

Moreover, the trophoblast or part thereof may be removed from the blastocyst by washing the blastocyst with a suitable medium such as SNUnt-2, G2.2 or S2. In such case, the trophoblast may be removed by a mechanical method known in the art, e.g., pipetting a solution containing the blastocyst using a pipette having a small bore.

Through these steps, the trophoblast is removed from the blastocyst; and the ICMs, i.e., the remaining part thereof, are obtained.

Step 7: Culturing of ICMs on Fibroblast Feeder Layer

ICMs isolated in step 6 are cultured on a fibroblast feeder layer since ICMs maintain their undifferentiated state when cultured on the fibroblast feeder layer. Sometimes, hLIF has been suggested for maintaining the undifferentiated morphology of ICMs instead of the feeder layer. However, it is practically impossible for a human cell to remain in its undifferentiated state without using a fibroblast feeder layer. Accordingly, the condition that does not induce extraembryonic differentiation and apoptosis in the ES cells generally requires culturing on a fibroblast feeder layer.

It is preferable to employ a mouse- and/or a human-derived fibroblast for preparing the fibroblast feeder layer. They may be used alone or in a mixture. It is more preferable to use cells differentiated from the ES cells derived from an autologous nucleus-transferred oocyte of a human as a feeder layer (this feeder layer has been designated as "auto feeder layer"). It is most preferable to use the fibroblasts differentiated from the ES cells derived from an autologous nucleus-transferred oocyte of an individual. The use of such feeder layer can prevent other foreign cells from contaminating the ES cells.

Such human-derived fibroblasts are capable of inducing an optimum growth and differentiation inhibition of the ES cells when appropriately mixed with mouse-derived fibroblasts.

The cell density in the fibroblast feeder layer may affect its stability and capability. In case of using a mixture of mouse and human fibroblasts, it is preferable to maintain the human fibroblasts at a density of, e.g., $2.5 \times 10^4$ cells/cm$^2$ and the mouse fibroblasts at a density of, e.g., $7.0 \times 10^4$ cells/cm$^2$. In case of using the mouse fibroblasts alone, it is preferable to use the same at a density ranging from $7.5 \times 10^4$ to $1.0 \times 10^5$ cells/cm$^2$. It is preferable to establish such feeder layer 6 to 48 hours before the addition of ES cells thereon.

Further, it is preferable to use mouse or human fibroblasts having a low passage number. Quality of the fibroblasts may affect the capability of supporting the ES cells. It is preferable to use the fibroblasts isolated from an embryo. The mouse fibroblasts are preferably obtained from 13.5-day old fetus, and the human fibroblasts, from an embryo or a fetal tissue. These fibroblasts can be cultured by using a cell culturing method known in the art.

In handling the mouse embryonic fibroblasts, it is important to minimize the use of trypsin and inhibit overcrowding. Otherwise, the mouse embryonic fibroblasts cannot support the growth of undifferentiated ES cells. Each batch of the mouse embryonic fibroblasts so prepared has to be tested first to confirm whether it is suitable for supporting and maintaining the ES cells.

Between fresh primary embryonic fibroblasts and fibroblasts having undergone a freezing-thawing treatment, the former is normally considered more suitable for supporting renewal of the ES cells. However, certain batches may show their capability of supporting the ES cells even after repeated freezing-thawing.

Certain mouse strains can produce embryonic fibroblasts more suitable for supporting the ES cells than other strains. For example, it has been demonstrated that the fibroblasts derived from the mice produced by inbreeding of 129/Sv or CBA strain or by crossbreeding of 129/Sv and C57/B16 strains are more suitable for supporting the ES cells.

In addition, it is preferable to inhibit the growth of feeder cells by using any one of the methods known in the art, including irradiation and chemical treatment. In a preferred embodiment, such cells are treated with mitomycin C.

The fibroblast feeder layer thus prepared is cultured on a petri dish coated with gelatin, preferably 0.1% gelatin.

The fibroblast feeder layer may be maintained in an ES medium. A suitable ES medium is the DMEM/F12 medium comprising 20% serum replacement, 0.1 mM β-mercaptoethanol, 1% NEAAs, 2 mM glutamine, 100 units/ml penicillin, and 100 μg/ml streptomycin, and 4 ng/ml human recombinant fibroblast growth factor (FGF).

Further, such ES medium may be supplemented with a soluble growth factor capable of stimulating growth or survival of the stem cells or inhibiting differentiation thereof. Representative examples of the growth factor are human pluripotent stem cell factor, ES cell renewal factor, and the like.

The isolated ICMs may be cultured for 6 days or longer, and cell colonies are generated therefrom. The colonies typically comprise undifferentiated stem cells. The undifferentiated stem cells may be isolated by using one of the methods known in the art. It is preferable to use a micropipette for isolating the undifferentiated stem cells. Such mechanical isolation may be supplemented with a treatment of a $Ca^{2+}/Mg^{2+}$-free PBS medium or an enzyme helpful for cell dissociation such as dispase.

Step 8: Subculturing of ES Cells

The ES cells cultured in step 7 are detached from the feeder layer and transferred to a fresh feeder layer. Then, the ES cells may be further cultured to propagate in a morphologically undifferentiated state.

In this case, it is preferable to culture the ES cells for 5 to 7 days. Undifferentiated stem cell colonies start to be observed by about the second day of culturing. The stem cells are morphologically identified by a high ratio in nucleus to cytoplasm, clear nucleoli, condensed colony formation and distinctive cell boundary.

Propagation of the undifferentiated stem cells is initiated by isolating an undifferentiated stem cell clump from the stem cell colony. Such isolation may be carried out by using one of the methods known in the art, such as a chemical or mechanical method. Preferably, the stem cells are isolated from the colony by washing with a $Ca^{2+}/Mg^{2+}$-free PBS medium, a mechanical method, or a combination thereof. It is more preferable to mechanically isolate the stem cells from the colony.

In a preferred embodiment, the $Ca^{2+}/Mg^{2+}$-free PBS medium may be used for reducing intercellular adhesive power. After incubation in the above medium for about 15 to 20 minutes, the cells begin to detach themselves gradually from the feeder layer, and, finally, are isolated as a clump having a desired size. In case such isolation of the cells proves to be insufficient, a mechanical method using a sharp edge of a micropipette may be more effectively employed for isolating and cutting the clump.

A chemical method employing an enzyme may be also used. The enzyme, preferably, dispase, may be used alone or in combination with a mechanical method.

In another preferred embodiment, it is possible to isolate clumps from the colony by treating with dispase after mechanical cutting of the colony. Cutting of the colony is carried out in a $Ca^{2+}/Mg^{2+}$-containing PBS medium. The colony can be mechanically cut into clumps, each clump containing about 100 cells, with the aid of a sharp edge of a micropipette. As soon as a clump is isolated, it is picked up with a micropipette having a wider bore, washed with the $Ca^{2+}/Mg^{2+}$-containing PBS medium, and transferred to a fresh fibroblast feeder layer.

It is necessary to confirm whether the stem cells maintain their undifferentiated state during these culturing processes. Undifferentiated stem cells can be identified by examining their typical morphological characteristic features as described above. Such stem cells can be also identified by detecting a cell marker or measuring the gene expression specific for a pluripotent cell.

Representative examples of genes specific for a pluripotent cell or a typical lineage include, but are not limited to, alkaline phosphatase, Octamer-4 (Oct-4), SSEA-3 and SSEA-4 which may be used as stem cell markers. Other exemplary genes specific for stem cells may include genesis, GDF-3 and cripto. The expression profile of these genes can be analyzed by using one of the methods known in the art, including reverse transcription-polymerase chain reaction (RT-PCR), a differentiation gene expression method, a microarray assay, and the like.

Preferably, the stem cells can be identified by an immunological reaction with a human pluripotent stem cell marker such as SSEA-4, germ cell tumor marker-2 (GCTM-2) antigen, TRA-1-60, or the like. In particular, the stem cells may express Oct-4 as a transcription factor and maintain a normal diploid karyotype.

Growth progress of the stem cells and maintenance status of their differentiated or undifferentiated state can be monitored by quantitatively measuring the proteins specific for the stem cells excreting into the medium or analyzing fixed cell preparations with enzyme-linked immunosorbent assay. Representative examples of the proteins specific for the stem cells are a soluble type of CD antigen and GCTM-2 antigen, and these proteins can be monitored by detecting a cell marker or measuring the gene expression.

In accordance with another aspect of the present invention, a nerve cell or a neuro progenitor is differentiated from an ES cell line derived from a nucleus-transferred oocyte prepared by transferring a nucleus of a human somatic cell into an enucleated human oocyte.

In accordance with a further aspect of the present invention, there is provided a method for preparing a neuro progenitor differentiated from an ES cell line derived from a nucleus-transferred oocyte prepared by transferring a nucleus of a human somatic cell into an enucleated human oocyte, which comprises the steps of:

(1) culturing the ES cell line to form an embryoid body;
(2) culturing the embryoid body in the presence of an agent suitable for differentiating a cell of the embryoid body into the neuro progenitor; and
(3) selecting a cell expressing a marker of the neuro progenitor and culturing the selected cell to obtain the neuro progenitor.

Hereinafter, the inventive method for preparing the neuro progenitor from the ES cell line is described in detail.

Step A: Preparation of an Embryoid Body

The first step for differentiating the ES cells derived from the nucleus-transferred oocytes (referred to as "nuclear transfer embryonic stem cells" or "ntES cells") into neuro progenitors is to generate an embryoid body by culturing the ES cells. The embryoid body can be prepared from the ES cells by using one of the methods known in the art (Zhang et al., *Nat. Biotechnol.*, 19:1129-1133 (2001)).

In a preferred embodiment, the embryoid body is obtained by transferring cultured ntES cell colonies into a non-adhesive culture dish containing the DMEM/F12 medium supplemented with a 20% serum replacement and culturing them for 3 to 5 days. Typically, floating embryoid bodies start to appear about one day after the beginning of the culturing (about 40 to 60 embryoid bodies/dish). At this point, it is preferable to transfer such embryoid bodies to a new dish while removing any remaining feeder cells. Then, the embryoid bodies are plated on an adhesive dish coated with polyornithine/laminin.

Step B: Inducement of Differentiation into Neuro Progenitors by an Agent

Representative agents which may be employed in the present invention for inducing differentiation of the embryoid bodies obtained in step A into neuro progenitors include, but are not limited to, retinoic acid; ascorbic acid; nicotinamide; N-2 supplement (100X, 17502-048; Gibco, Grand Island, N.Y., U.S.A.); B-27 supplement (50X, 17504-044, Gibco, Grand Island, N.Y., U.S.A.); and a mixture of insulin, transferrin, sodium selenite and fibronectin (ITSF). Neuro progenitors differentiated from the ntES cells can be obtained by culturing the embryoid bodies in a medium supplemented with such agent and inducing their expansion and differentiation.

In a preferred embodiment, the embryoid bodies prepared in step A are further cultured for 1 day followed by culturing in the DMEM/F12 medium supplemented with ITSF, i.e., insulin (about 25 µg/ml), transferrin (about 100 µg/ml), sodium selenite (about 30 nM) and fibronectin (about 5 µg/ml) for 5 to 10 days, thereby inducing differentiation of the ntES cells into the neuro progenitors.

Step C: Selection and Culturing of Cells Expressing a Neuro Progenitor Marker

The neuro progenitors differentiated from the ntES cells may be obtained by selecting cells expressing a neuro progenitor marker such as nestin among the differentiated cells obtained in step B and culturing them.

Further, the obtained neuro progenitors may be differentiated into desired specific type of nerve cells. The differentiation into the nerve cells can be carried out through conventional methods such as induction with chemicals, etc.

In a preferred embodiment, the cells exhibiting a positive signal for a neuro progenitor marker are selected; their expansion is induced by culturing the selected cells in the DMEM/F12 medium supplemented with the N-2 supplement, laminin and basic fibroblast growth factor (bFGF) for 5 to 7 days; and, then, they are further cultured in the DMEM/F12 medium supplemented with only the N-2 supplement and laminin for 8 to 14 days.

It is well known that ES cells are capable of differentiating into almost any type of cells. Accordingly, the ES cell line of the present invention may be a good source providing various types of cells. For instance, the ES cells may be induced to differentiate into hematopoietic cells, nerve cells, beta cells, muscle cells, liver cells, cartilage cells, epithelial cells, etc., by culturing them in a medium under conditions suitable for cell differentiation. Such medium and conditions are well known in the art.

Accordingly, the ES cell line of the present invention may have numerous therapeutic and diagnostic applications. Especially, such ES cell line may be used in cell transplantation therapies for the treatment of numerous diseases, e.g., diabetes, Parkinson's disease, Alzheimer's disease, amyotrophic lateral sclerosis (ALS), cerebral palsy and cancer. Further, the ES cell line derived from the autologous nucleus-transferred oocyte can be advantageously used in the cell transplantation therapies since no adverse immunorejection reaction may occur during and after the treatment procedure.

The following Examples are intended to further illustrate the present invention without limiting its scope.

The G1.2 medium or G1 ver.3 medium (Vitro Life, Goteborg, Sweden) used in these Examples are supplemented with 5% HSA unless indicated otherwise.

EXAMPLE 1

Preparation of Oocyte and Nuclear Donor Cell

Voluntary oocyte donors were screened carefully through physical and mental examinations, and administered with follicle stimulation hormone (FSH) to induce superovulation.

About 36 hours after the administration of human chorionic gonadotropin (hCG) to the donors, cumulus-oocyte complexes (COCs) were recovered and cultured for 40 minutes in the G1.2 medium using an incubator maintained at 37° C., 5% $CO_2$ and saturated humidity. Such COCs were treated with 0.1% (w/v) hyaluronidase (Sigma Co., St. Louis, Mo., U.S.A.) for 1 hour to disperse cumulus cells.

The oocytes were obtained by separating such cumulus cells from the COCs. The separated cumulus cells were isolated through a mouth pipette and washed with the G1.2 medium. Those cumulus cells having a modal diameter ranging from 10 to 12 mm were selected as nuclear donor cells.

EXAMPLE 2

Enucleation of Oocyte and Cell Fusion

One of the oocytes obtained in Example 1 was cultured in the G1.2 medium for 1 to 2 hours in order to induce the maturation of its nucleus. Thereafter, enucleation, nuclear transfer and electrofusion thereof were performed as follows.

(2-1) Enucleation of Oocyte and Nuclear Transfer from Somatic Cell

The oocyte was washed once with the G1.2 medium. Such oocyte was transferred to a hyaluronidase solution prepared by mixing 1 ml of the G1.2 medium with 111 µl of a solution, wherein 0.05 g of hyaluronidase was dissolved in 5 ml of the G1.2 medium, and adjusted to a 0.1% (w/v) hyaluronidase concentration. The oocyte was stripped of any remaining cumulus cells, washed three times with the G1.2 medium and placed in the same medium. Then, the oocyte was transferred to a cytochalasin B solution prepared by mixing 1 ml of the G1.2 medium supplemented with 10% fetal bovine serum (FBS) with 1 µl of a solution wherein cytochalasin B was dissolved in dimethyl sulfoxide to a concentration of 7.5 µg/ml. The zona pellucida of the oocyte was incised by a micromanipulator to form a small hole, and the oocyte was enucleated by removing part of the cytoplasm containing the first polar body thereof and corresponding to 10 to 15% of the total cytoplasm through the small hole.

Figure 3:
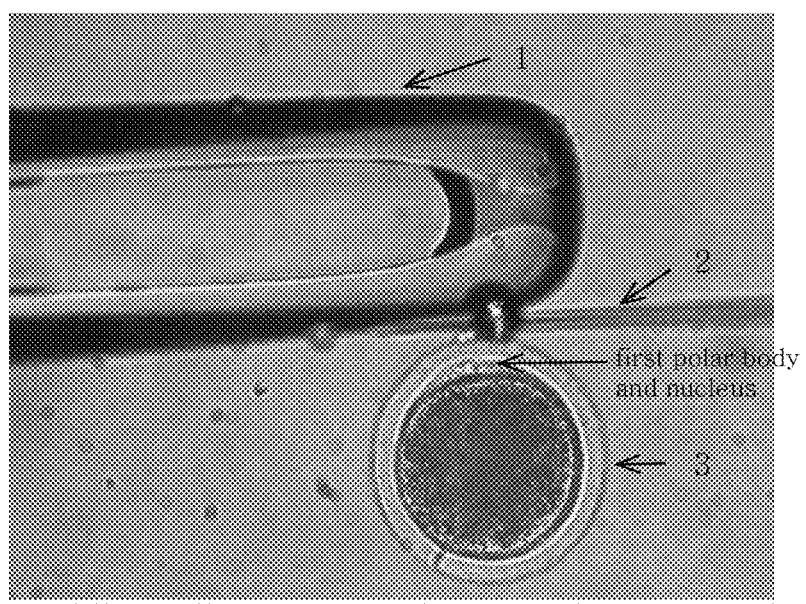
FIG. 3 depicts the incision process of the zona pellucida of an oocyte (3) with a holding pipette (1) and an incision pipette (2)
Figure 4:
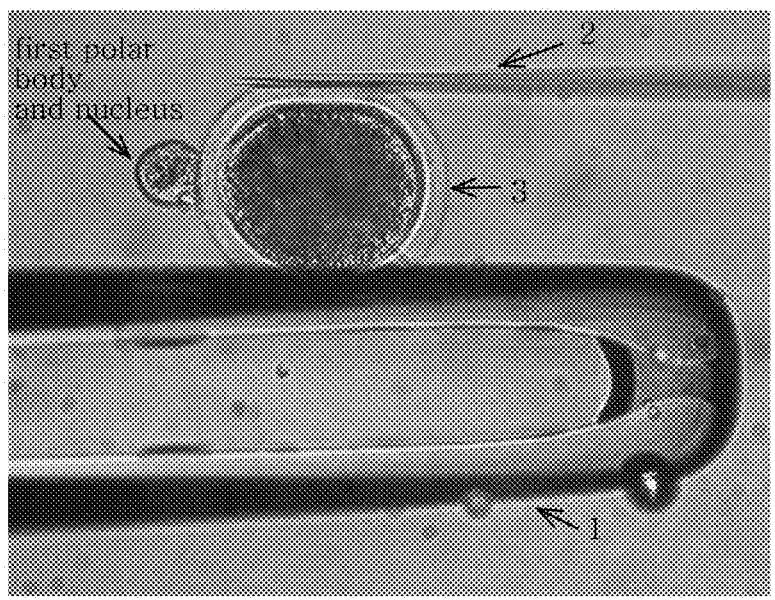
FIG. 4 presents a photograph showing the removal of the first polar body and the nucleus of the oocyte (3) with the holding pipette (1) and the incision pipette (2)

FIG. 3 shows the incision process of the zona pellucida of the oocyte (3) by employing a holding pipette (1) and an incision pipette (2). FIG. 4 shows the enucleation process removing the first polar body and the nucleus from the oocyte where the oocyte (3) having the small hole vertically positioned was supported by the holding pipette (1) positioned beneath the oocyte and then lightly pressed by the incision pipette (2) to enucleate the same. Such enucleated oocyte was washed three times with the G1.2 medium and placed in the same medium.

Subsequently, a nuclear donor cell in a 4 µl drop of PBS supplemented with 1% BSA was transferred, using a holding pipette and a transfer pipette, into the enucleated oocyte in a 4 µl drop of a solution prepared by mixing 400 µl of the G1.2 medium with 100 µl of a PHA-P solution wherein 5 mg of PHA-P was dissolved in 10 ml of the G1.2 medium. The drops containing the nuclear donor cell and the enucleated oocyte were coated with a mineral oil to prevent the evaporation of the drops.

Figure 5:
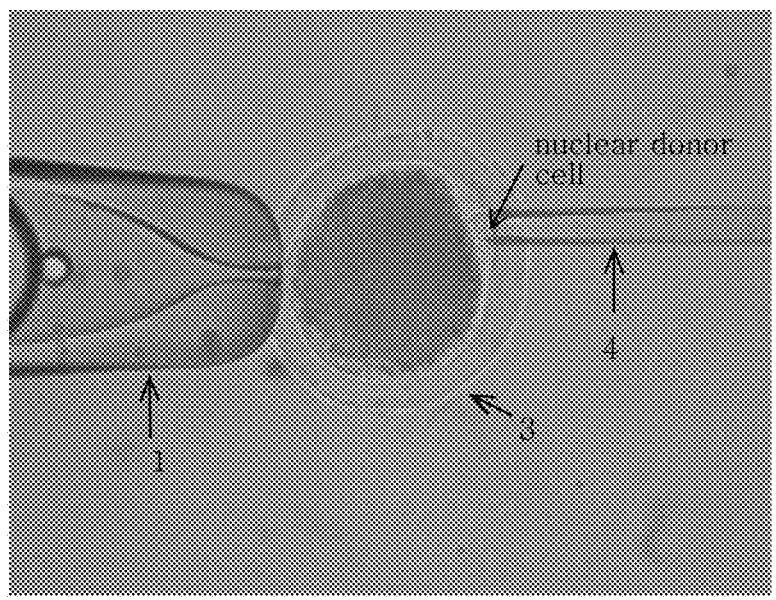
FIG. 5 offers a photograph showing the transfer of a nuclear donor cell into an enucleated recipient oocyte (3) with the holding pipette (1) and a transfer pipette (4)

FIG. 5 describes the process used to transfer the nuclear donor cell into the enucleated oocyte. As can be seen from FIG. 5, the enucleated oocyte (3) was fixed to a holding pipette (1), a transfer pipette (4) was injected through the small hole into the enucleated oocyte (3) and, then, the nuclear donor cell was injected into the oocyte (3) to obtain a nucleus-transferred oocyte. Such nucleus-transferred oocyte was washed three times with the G1.2 medium and placed in the same medium.

(2-2) Preparation of Nucleus-Transferred Oocyte by Electrofusion

The nucleus-transferred oocyte was subjected to electrofusion through a BTX-electro cell manipulator (BTX Inc., San Diego, Calif., U.S.A.).

A 20 µl drop of a mannitol solution prepared by dissolving 0.1 mM $MgSO_4$, 0.05% BSA and 0.28 mM mannitol in a 0.5 mM HEPES buffer (pH 7.2), a 20 µl drop of a mixing solution containing 10 µl of the G1.2 medium and 10 µl of the mannitol solution, and a 20 µl drop of the G1.2 medium were prepared.

First, the nucleus-transferred oocyte obtained in Example (2-1) was incubated in the 20 µl drop of the mixing solution for 1 minute. Next, the nucleus-transferred oocyte was transferred to the 20 µl drop of the mannitol solution via a mouth pipette and incubated therein for 1 minute. Subsequently, the nucleus-transferred oocyte was transferred to a mannitol solution having the above composition and placed between two electrodes connected to the BTX-electro cell manipulator and was positioned such that the nuclear donor cell faced the (+) electrode. The nucleus-transferred oocyte was electrofused by applying a direct current of 1 kV/cm for 15 µs twice, at an interval of 1 second.

The fused nucleus-transferred oocyte was incubated in the 20 µl drop of the mixing solution for 1 minute, transferred to the 20 µl drop of the G1.2 medium and then washed with the G1.2 medium three times.

EXAMPLE 3

Reprogramming, Activation and In Vitro Culturing of Nucleus-Transferred Oocyte

Since a sperm-mediated activation, which is one of the major factors for a normal embryonic development, was absent in case of the nucleus-transferred oocyte obtained in Example 2, an artificial stimulus was needed instead. In order to determine the optimum conditions for artificial embryogenesis, therefore, nucleus-transferred oocytes were reprogrammed, activated and in vitro cultured under various conditions as shown in Tables 2 to 4.

First, to examine the effect of the reprogramming time on the rate of blastocyst formation, the reprogramming times were set at about 2, 4, 6 and 20 hours, respectively, while applying the same conditions for activation and in vitro culturing as can be seen from Table 2. As a result, the highest rate of blastocyst formation was obtained when the reprogramming time was about 2 hours.

TABLE 2

| Reprogramming time (hour) | Activation condition | | In vitro culture condition | | No. of oocytes | No. of nucleus-transferred oocytes developed to | | |
|---|---|---|---|---|---|---|---|---|
| | | | $1^{st}$ medium | $2^{nd}$ medium | | 2-cell stage | morula | blastocyst |
| 2 | 10 μM ionophore* | 2.0 mM 6-DMAP | G1.2 | SNUnt-2 | 16 | 16 | 4 | 4 |
| 4 | 10 μM ionophore* | 2.0 mM 6-DMAP | G1.2 | SNUnt-2 | 16 | 15 | 1 | 0 |
| 6 | 10 μM ionophore* | 2.0 mM 6-DMAP | G1.2 | SNUnt-2 | 16 | 15 | 1 | 1 |
| 20 | 10 μM ionophore* | 2.0 mM 6-DMAP | G1.2 | SNUnt-2 | 16 | 9 | 1 | 0 |

*calcium ionophore A23187

Next, to find the optimal activation condition for blastocyst formation, nucleus-transferred oocytes subjected to about 2 hour-reprogramming time were treated for 5 minutes with calcium ionophore A23187 (5 or 10 μM; Sigma Co., St. Louis, Mo., U.S.A.) or ionomycin (5 or 10 μM; Sigma Co., St. Louis, Mo., U.S.A.) in the G1.2 medium at 37° C. as can be seen from Table 3. Such nucleus-transferred oocytes were washed several times with the G1.2 medium, transferred to the G1.2 medium containing 2.0 mM 6-DMAP (Sigma Co., St. Louis, Mo., U.S.A.) and, then, cultured at 37° C., 5% $CO_2$, 5% $O_2$ and 90% $N_2$ for 4 hours. After these activation steps, the nucleus-transferred oocytes were in vitro cultured under the same condition. As can be seen from Table 3, the highest rate of blastocyst formation was observed when the oocyte was sequentially treated with 10 μM calcium ionophore and 2.0 mM 6-DMAP.

cultured for 48 hours in a 100 drop of the G1.2 medium or SNUnt-2 medium at 37° C. in 5% CO2, 5% O2 and 90% N2 atmosphere. After such culturing, the nucleus-transferred oocytes were transferred to a fresh SNUnt-2 medium or G2.2 medium and cultured further for 6 days. A representative example of the in vitro culture medium is the G2.2 medium (Vitro Life, Goteborg, Sweden) comprising Alanine, Alanyl-glutamine, Arginine, Asparagine, Aspartic acid, Calcium chloride, Calcium pantothenate, Choline chloride, Cystine, Folic acid, Glucose, Glutamic acid, Glycine, Histidine, Human serum albumine, Inositol, Isoleucine, Leucine, Lysine, Magnesium sulphate, Methionine, Nicotinamide, Penicillin G, Phenylalanine, Potassium chloride, Proline, Pyridoxal HCL, Riboflavin, Serine, Sodium bicarbonate, Sodium chloride, Sodium dihydrogen phosphate, Sodium lactate, Sodium pyruvate, Thiamine, Threonine, Tryptophan, Tyrosine, Valine and water.

TABLE 3

| Reprogramming time (hour) | Activation condition | | In vitro culture condition | | No. of oocytes | No. of nucleus-transferred oocytes developed to | | |
|---|---|---|---|---|---|---|---|---|
| | | | $1^{st}$ medium | $2^{nd}$ medium | | 2-cell stage | morula | blastocyst |
| 2 | 5 μM ionophore* | 2.0 mM 6-DMAP | G1.2 | SNUnt-2 | 16 | 11 | 0 | 0 |
| 2 | 10 μM ionophore* | 2.0 mM 6-DMAP | G1.2 | SNUnt-2 | 16 | 16 | 5 | 3 |
| 2 | 5 μM ionomycin | 2.0 mM 6-DMAP | G1.2 | SNUnt-2 | 16 | 9 | 0 | 0 |
| 2 | 10 μM ionomycin | 2.0 mM 6-DMAP | G1.2 | SNUnt-2 | 16 | 12 | 0 | 0 |

*calcium ionophore A23187

Finally, the optimal in vitro culture condition was determined as follows: The nucleus-transferred oocytes subjected to the above optimal reprogramming and activation conditions were washed vigorously with the G1.2 medium and As indicated in Table 4, the highest rate of blastocyst formation was detected when the oocyte was first cultured in the G1.2 medium and subsequently in the SNUnt-2 medium.

TABLE 4

| Reprogramming time (hour) | Activation condition | | In vitro culture condition | | No. of oocytes | No. of nucleus-transferred oocytes developed to | | |
|---|---|---|---|---|---|---|---|---|
| | | | $1^{st}$ medium | $2^{nd}$ medium | | 2-cell stage | morula | blastocyst |
| 2 | 10 μM ionophore* | 2.0 mM 6-DMAP | G1.2 | SNUnt-2 | 16 | 16 | 4 | 3 |
| 2 | 10 μM ionophore* | 2.0 mM 6-DMAP | G1.2 | G2.2 | 16 | 16 | 0 | 0 |

TABLE 4-continued

| Reprogramming | | In vitro culture condition | | | No. of nucleus-transferred oocytes developed to | | |
|---|---|---|---|---|---|---|---|
| time (hour) | Activation condition | 1st medium | 2nd medium | No. of oocytes | 2-cell stage | morula | blastocyst |
| 2 | 10 μM ionophore* 2.0 mM 6-DMAP | SNUnt-2 | SNUnt-2 | 16 | 16 | 0 | 0 |

*calcium ionophore A23187

Based on the above results, an optimal embryogenesis of a nucleus-transferred oocyte was achieved by subjecting the oocyte to 2-hour reprogramming, activation through a serial treatment with 10 μM calcium ionophore and 2.0 mM 6-DMAP, and a sequential culturing in the G1.2 medium and the SNUnt-2 medium.

Under the above optimal conditions, additional 66 nucleus-transferred oocytes were reprogrammed, activated and in vitro cultured to thereby yield 19 blastocysts (equal to 29%). This percentage of the nucleus-transferred oocytes developed to blastocysts in accordance with the present invention is comparable to those observed in established SCNT methods in cattle (about 25%) (Kwun et al., *Mol. Reprod. Dev.*, 65:167-174 (2003)) and pigs (about 26%) (Hyun et al., *Biol. Reprod.*, 69:1060-1068 (2003); Kuhholzer et al., *Biol. Reprod.*, 64:1635-1698 (2004)).

EXAMPLE 4

Removal of Zona Pellucida and Trophoblast, and Isolation of ICMs

The blastocyst obtained in Example 3 was treated with 0.1% pronase (Sigma Co., St. Louis, Mo., U.S.A.) for 1 minute to remove its zona pellucida. Then, it was treated with 100% anti-human serum antibody (Sigma Co., St. Louis, Mo., U.S.A.) for 20 minutes, and was exposed to 10 μl of guinea pig complement (Life Technologies, Rockville, Md., U.S.A.) at 37° C., 5% $CO_2$ for 30 minutes to remove its trophoblast and isolate ICMs therefrom.

EXAMPLE 5

Culturing of ICMs

The ICMs isolated in Example 4 were cultured in a tissue culture dish coated with 0.1% gelatin, which contained a feeder layer (7.5×10⁴ cells/cm²) of mitomycin C-inactivated primary mouse (C57BL breed) embryonic fibroblasts. DMEM/F12 medium (Life Technologies, Rockville, Md., U.S.A.) comprising 20% serum replacement, 0.1 mM β-mercaptoethanol, 1% NEAAs, 2 mM glutamine, 100 units/ml penicillin, and 100 μg/ml streptomycin, and 4 ng/ml bFGF (Life Technologies, Rockville, Md., U.S.A.) was used as the culture medium.

At an early stage of culturing the ES cells in the ICMs, the medium was supplemented with a hLIF (100 units/ml; Chemicon, Temecula, Calif., U.S.A.). The culturing was conducted for more than 6 days until the colonies of undifferentiated ntES cells appeared. The ntES cells were mechanically isolated from the colonies by using a micropipette every five or seven days after such colony formation.

The ntES cell line thus obtained from the nucleus-transferred oocyte prepared by transferring a nucleus of a female somatic cell into an enucleated human oocyte was designated "hntES" and deposited with the Korean Cell Line Research Foundation (KCLRF; Address: Cancer Research Institute, College of Medicine, Seoul National University, 28, Yongon-dong, Chongno-gu, Seoul 110-744, Republic of Korea) on Dec. 29, 2003 under the accession number of KCLRF-BP-00092, in accordance with the terms of the Budapest Treaty on the International Recognition of the Deposit of Microorganisms for the Purposes of Patent Procedure.

TEST EXAMPLE 1

Identification of Human ntES Cells Obtained in Example 5 by Karyotype Analysis

The colonies of the undifferentiated ntES cells obtained in Example 5 were washed with PBS containing 0.1 mM $Ca^{2+}$ and 0.1 mM $Mg^{2+}$, fixed with citrate-acetone-formaldehyde (the mixing ratio in volume was 25:65:8) at 4° C. for 1 hour, and washed again with PBS containing 0.1 mM $Ca^{2+}$ and 0.1 mM $Mg^{2+}$. The alkaline phosphatase activity of the ntES cells was determined by AP kit (Sigma Co., St. Louis, Mo., U.S.A.). Further, an immunohistochemical assay was performed in order to identify specific surface antigens on the ntES cells, by employing monoclonal antibodies Oct-4 (SC-5279) purchased from Santa Cruz Biotechnology (Santa Cruz, Calif., U.S.A.); SSEA-1 (MC480), SSEA-3 (MC631) and SSEA-4 (MC-813-70) purchased from Developmental Studies Hybridoma Bank (Iowa City, Iowa, U.S.A.); and TRA-1-60 and TRA-1-80 purchased from Chemicon (Temecula, Calif., U.S.A.) as primary antibodies. Such primary antibodies were detected by using a Vectastatin ABC kit (Vector laboratory, Burlingame, Calif., U.S.A.) containing a biotinylated secondary antibody and an avidin-horseradish peroxidase conjugate.

DNA fingerprinting analysis was performed with regard to the genomic DNA and human short tandem repeat (STR) marker using a STR AMP FLSTR PROFILER kit (Applied Biosystems, Foster City, Calif., U.S.A.) with an automated ABI 310 Genetic Analyzer (Applied Biosystems, Foster City, Calif., U.S.A.). The results are shown in FIGS. 6A to 6D.

As shown in FIGS. 6A to 6D, it was observed that the karyotype of the ntES cells derived from the nucleus-transferred oocyte prepared in accordance with Examples 1 to 5 above was identical to that of the nuclear donor cell. This result demonstrates that the ntES cells of the present invention have been indeed derived from the nucleus-transferred oocyte prepared by transferring a nucleus of a female somatic cell into an enucleated human oocyte, not from a parthenogenetically activated oocyte.

TEST EXAMPLE 2

Identification of Human ntES Cells by Teratoma Analysis 100 colonies of the undifferentiated ntES cells obtained in Example 5 were isolated from their culture dish, injected into a testis of a SCID mouse (Korea Research Institute of Bioscience and Biotechnology, Korea) using a 1 ml syringe and cultured for 8 weeks. Teratomas thus formed were paraffin-fixed and examined by an immunohistochemical assay to check whether three dermal cells were formed. The result is shown in FIG. 7.

Figure 7:
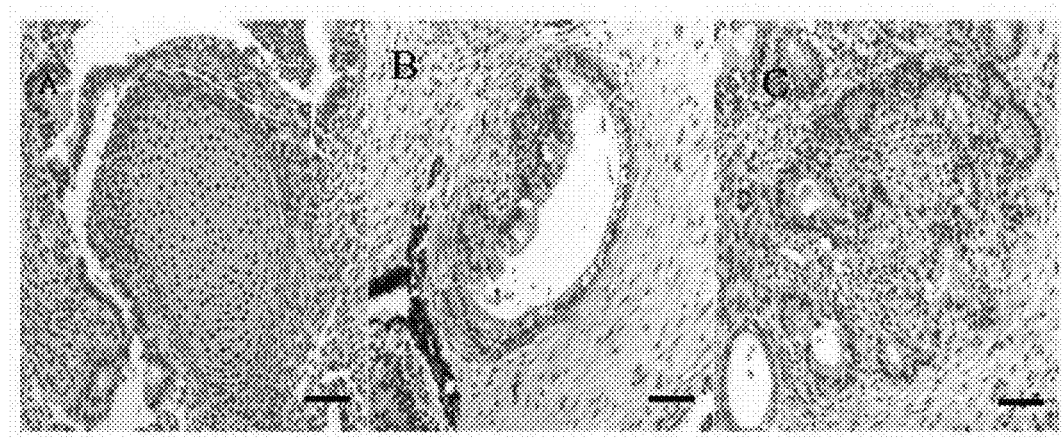
FIG. 7 illustrates three types of blastodermal cells identified within a teratoma formed by injecting an undifferentiated cell colony obtained in accordance with the present invention into a gonad of an immune deficiency mouse (A: cartilage, B: intestinal tract, C: neural tube (A,B,C: ×200))

As indicated in FIG. 7, it was found that the ntES cells obtained in Example 5 formed three dermal cells (cartilage (A): endoderm; intestinal tract (B): mesoderm; neural tube (C): ectoderm) in the testis. This result demonstrates that such ntES cells are pluripotent ES cells having the ability to differentiate into various tissues.

TEST EXAMPLE 3

Examination of Embryoid Body Formation Through Immunohistochemical Assay

Colonies of the human ntES cells obtained in Example 5 were treated with 0.1% trypsin/1 mM EDTA to isolate the ntES cells, which were then transferred to a plastic petri dish. The human ntES cells were cultured for 14 days in the DMEM/DMEM F12 medium devoid of hLIF and bFGF. For paraffin fixation, such ntES cells were transferred to 1% low-melting temperature agarose dissolved in PBS and cooled to 42° C. The resulting solidified agarose containing the ntES cells was fixed by 4% paraformaldehyde dissolved in PBS and embedded in paraffin. Each 6-mm section of the paraffin-embedded cells was placed on a slide and subjected to an immunohistochemical analysis. As primary antibodies, alpha-1-fetoprotein (18-0003), cytokeratin (18-0234), desmin (18-0016), neurofilament (18-0171) and S-100 (18-0046) purchased from Zemed (South San Francisco, Calif., U.S.A.) and HNF-2-alpha (SC-6556), BMP-4 (SC-6896), Myo D (SC-760) and NCAM (SC-7326) purchased from Santa Cruz Biotechnology (Santa Cruz, Calif., U.S.A.) were employed. A biotinylated anti-rabbit, anti-mouse or anti-goat antibody was used as a secondary antibody, and the reaction was detected by streptavidin-conjugated horseradish peroxidase and diaminobenzidine chromagen. The result is shown in FIG. 8.

Figure 8:
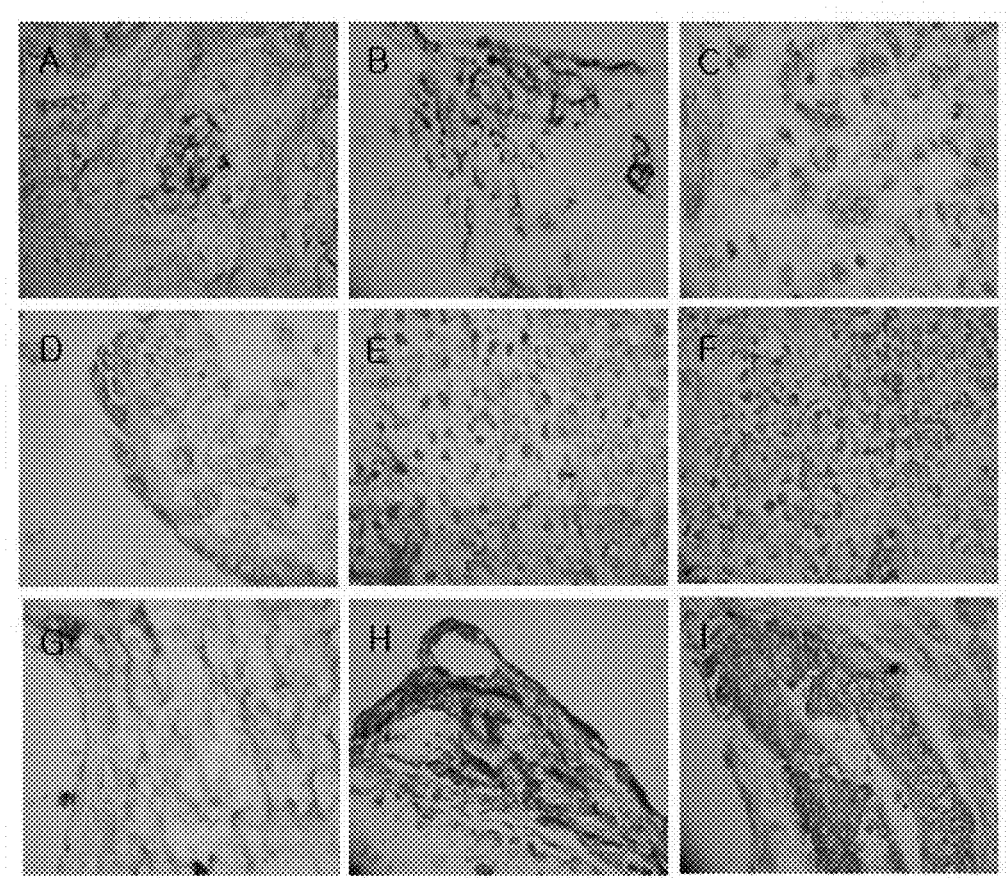
FIG. 8 provides photographs confirming the formation of an embryoid body from an ES cell line in accordance with the present invention (A,B,C: endoderm; D,E,F: mesoderm; G,H,I,: ectoderm; A: alpha-1-fetoprotein; B: cytokeratin; C: HNF-2-alpha; D: BMP-4; E: Myo D; F: desmin; G: neurofilament; H: S-100; and I: NCAM).

As shown in FIG. 8, it was confirmed that such ntES cells could form embryoid bodies based on the fact that the marker proteins of endoderm (i.e., alpha-1-fetoprotein (A), cytokeratin (B), and HNF-2-alpha (C)), the marker proteins of mesoderm (i.e., BMP-4 (D), Myo D (E), and desmin (F)) and the marker proteins of ectoderm (i.e., neurofilament (G), S-100 (H), and NCAM (I)) were expressed in the ntES cells obtained in Example 5. This result demonstrates that the cells obtained in the present invention fall within the scope of an ES cell.

EXAMPLE 6

Differentiation into Neuro Progenitors (6-1) Expansion of Undifferentiated ES Cells
The human undifferentiated ntES cells obtained in Example 5 were cultured at 37° C. in 5% $CO_2$ atmosphere on a mouse embryonic fibroblast feeder layer with inactivated cell division, contained in a culture plate coated with 2% gelatin. The culture medium was composed of DMEM/F12 (1:1), 20% knock-out serum replacement, 0.1 mM NEAAs, 0.1 mM β-mercaptoethanol, 1 mM L-glutamine, 100 U/ml penicillin G, 100 μg/ml streptomycin, and 4 ng/ml bFGF; and was changed everyday.

(6-2) Formation of Embryoid Body
Colonies of the ntES cells cultured as above were collected and cultured on a non-adhesive culture dish at 37° C. in 5% $CO_2$ atmosphere. The culture medium was identical to that of Example (6-1) except that 4 ng/ml bFGF was omitted therefrom. After one day, such colonies began to grow as floating embryoid bodies (about 50 embryoid bodies/dish). At that point, the embryoid bodies were transferred to a new dish, while removing any remaining feeder cells completely. After further culturing for 4 days, embryoid bodies thus formed were plated on an adhesive dish coated with poly-ornithine/laminin.

(6-3) Selection of Nestin-Positive Cells
After 1-day culturing on the adhesive dish, embryoid bodies in the process of differentiation were transferred to the DMEM/F12 medium supplemented with insulin (25 μg/ml), transferrin (100 μg/ml), sodium selenite (30 nM) and fibronectin (5 μg/ml) and cultured at 37° C. for 6 days. The resulting cells were cultured at 37° C. for 40 minutes in a solution wherein anti-nestin antibody (Chemicon, Temecula, Calif., U.S.A.) was diluted 1000 folds with a solution containing 0.01M PBS, 1% BSA and 5 mM EDTA. Such cells were washed with the DMEM/F12 medium, treated with phycoerythrine (PE)-conjugated secondary antibody (Chemicon, Temecula, Calif., U.S.A.) for 30 minutes and then washed three times with the DMEM/F12 medium, thereby selecting the nestin-positive cells.

(6-4) Expansion of Nestin-Positive Cells
The nestin-positive cells selected in Example (6-3) were cultured at 37° C. in the DMEM/F12 medium supplemented with the N-2 supplement, laminin (1 ng/ml) and bFGF (10 ng/ml) for 6 days to expand those cells.

(6-5) Differentiation into Neuro Progenitors
The nestin-positive cells expanded in Example (6-4) were cultured for 10 days at 37° C. in the DMEM/F12 medium supplemented with the N-2 supplement and laminin (1 ng/ml) but devoid of bFGF to induce their differentiation into neuro progenitors.

Figure 2:
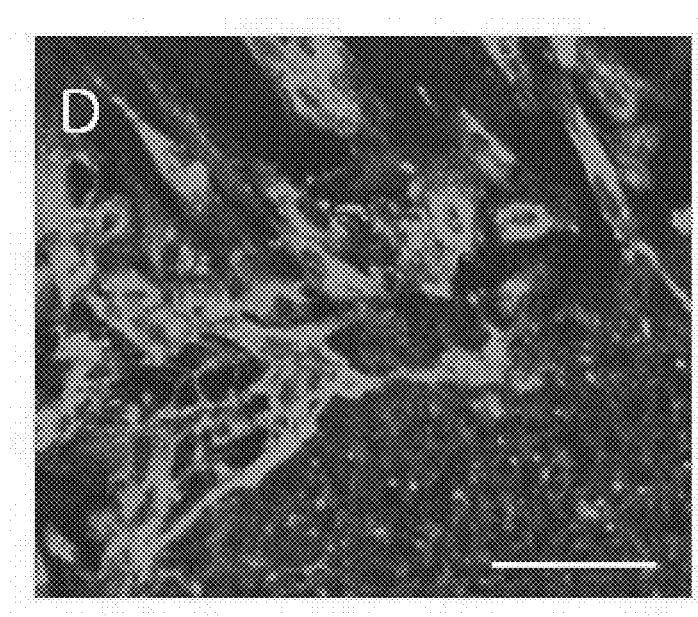
FIG. 2 represents a photograph of a fluorescence-stained neuro progenitor differentiated from an undifferentiated colony obtained in accordance with the present invention by adding a mixture of insulin, transferrin, sodium selenite and fibronectin (×400)

FIG. 2 shows the neuro progenitors differentiated from the nucleus-transferred oocyte prepared by transferring a nucleus of a female somatic cell into an enucleated human oocyte.

While the invention has been described with respect to the above specific embodiments, it should be recognized that various modifications and changes may be made to the invention by those skilled in the art which also fall within the scope of the invention as defined by the appended claims.

Indications Relating to Deposited Microorganism or Other Biological Material

What is claimed is:
1. A method for preparing a neuro progenitor, comprising the steps of:
   (1) culturing a human somatic cell to prepare a nuclear donor cell;
   (2) enucleating a human oocyte to prepare a recipient oocyte;
   (3) preparing a nucleus-transferred oocyte by transferring a nucleus of the nuclear donor cell into the recipient oocyte and fusing the nucleus of the nuclear donor cell and the recipient oocyte;
   (4) subjecting the nucleus-transferred oocyte to reprogramming, activation and in vitro culturing to form a blastocyst;
   (5) isolating an inner cell mass from the blastocyst and culturing the inner cell mass in an undifferentiated state to establish the embryonic stem cell line deposited under the accession number of KCLRF-BP-00092;

(6) culturing the embryonic stem cell line to form an embryoid body;
(7) culturing the embryoid body in the presence of an agent suitable for differentiating a cell of the embryoid body into the neuro progenitor; and
(8) selecting a cell expressing a marker of the neuro progenitor and culturing the selected cell to obtain the neuro progenitor,
wherein step (4) is performed by reprogramming the nucleus-transferred oocyte for a time period of up to 3 hours, treating the nucleus-transferred oocyte with a calcium ionophore at a concentration ranging from 6 μM to 15 μM and subsequently with 6-dimethylaminopurine at a concentration ranging from 1.5 mM to 2.5 mM, and sequentially culturing the nucleus-transferred oocyte in vitro in the G1.2 medium and the SNUnt-2 medium.

2. The method of claim 1, wherein the agent employed in step (7) is selected from the group consisting of retinoic acid; ascorbic acid; nicotinamide; N-2 supplement; B-27 supplement; and a mixture of insulin, transferrin, sodium selenite and fibronectin.

3. A medium for use in carrying out the in vitro culturing in step (4) of claim 1, comprising:
95 to 110 mM NaCl; 7.0 to 7.5 mM KCl; 20 to 30 mM NaHCO$_3$; 1.0 to 1.5 mM NaH$_2$PO$_4$; 3 to 8 mM sodium lactate; 1.5 to 2.0 mM CaCl$_2$.2H$_2$O; 0.3 to 0.8 mM MgCl$_2$.6H$_2$O; 0.2 to 0.4 mM sodium pyruvate; 1.2 to 1.7 mM fructose; 6 to 10 mg/ml human serum albumin; 0.7 to 0.8 μg/ml kanamycin; 1.5 to 3% essential amino acids; 0.5 to 1.5% nonessential amino acids; 0.7 to 1.2 mM L-glutamine; and 0.3 to 0.7% a mixture of insulin, transferrin and sodium selenite.

4. The medium of claim 3, which comprises:
99.1 to 106 mM NaCl; 7.2 mM KCl; 25 mM NaHCO$_3$; 1.2 mM NaH$_2$PO$_4$; 5 mM sodium lactate; 1.7 mM CaCl$_2$.2H$_2$O; 0.5 mM MgCl$_2$.6H$_2$O; 0.3 mM sodium pyruvate; 1.5 mM fructose; 8 mg/ml human serum albumin; 0.75 μg/ml kanamycin; 2% essential amino acids; 1% nonessential amino acids; 1 mM L-glutamine; and 0.5% a mixture of insulin, transferrin and sodium selenite.

* * * * *